(12) United States Patent
Mech et al.

(10) Patent No.: US 12,702,346 B2
(45) Date of Patent: Aug. 11, 2026

(54) SYSTEMS AND METHODS FOR VAGUS NERVE MONITORING AND STIMULATION

(71) Applicant: The Alfred E. Mann Foundation for Scientific Research, Valencia, CA (US)

(72) Inventors: Brian V. Mech, Buffalo, MN (US); Neil Talbot, La Crescenta, CA (US); Brian M. Shelton, Ventura, CA (US); Joseph L. Calderon, Santa Clarita, CA (US); Robert J. Greenberg, Los Angeles, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 646 days.

(21) Appl. No.: 18/167,041

(22) Filed: Feb. 9, 2023

(65) Prior Publication Data

US 2023/0248302 A1 Aug. 10, 2023

Related U.S. Application Data

(60) Provisional application No. 63/308,437, filed on Feb. 9, 2022.

(51) Int. Cl.

| | |
|---|---|
| ***A61B 5/24*** | (2021.01) |
| ***A61B 5/00*** | (2006.01) |
| ***A61B 5/369*** | (2021.01) |
| *A61B 5/0205* | (2006.01) |

(52) U.S. Cl.
CPC ............ *A61B 5/4094* (2013.01); *A61B 5/369* (2021.01); *A61B 5/0205* (2013.01)

(58) Field of Classification Search
CPC ...... A61B 5/4094; A61B 5/7264; A61B 5/369
See application file for complete search history.

(56) References Cited

U.S. PATENT DOCUMENTS

| | | | | |
|---|---|---|---|---|
| 11,428,955 | B1 | 8/2022 | Lewis | |
| 2020/0086122 | A1 | 3/2020 | Osorio | |
| 2021/0259621 | A1 * | 8/2021 | Alves .................. | A61B 5/4094 |
| 2021/0401356 | A1 | 12/2021 | Gluckman et al. | |
| 2022/0288398 | A1 | 9/2022 | Mech et al. | |
| 2022/0313159 | A1 | 10/2022 | Arcot Desai et al. | |

OTHER PUBLICATIONS

International Search Report and Written Opinion in PCT/US23/62328, mailed Jun. 27, 2023, 18 pages.
Kaminski et al., "A framework for sensitivity analysis of decision trees", Cejor (2018), vol. 26, pp. 135-159.
Prinzie et al., "Random Multiclass Classification: Generalizing Random Forests to Random MNL and Random NB", Database and Expert Systems Applications, Lecture Notes in Computer Science (2007), vol. 4653, pp. 349-358.

(Continued)

*Primary Examiner* — Michael J D'Abreu
(74) *Attorney, Agent, or Firm* — ARENTFOX SCHIFF LLP

(57) ABSTRACT

The present disclosure generally relates to devices, systems, and methods for detecting, monitoring, predicting, and/or treating medical conditions (e.g., epileptic seizures) using one or more sensors configured to collect biomarker data from a human subject (e.g., vagal tone and/or physiological or other biomarkers).

31 Claims, 4 Drawing Sheets

(56) References Cited

OTHER PUBLICATIONS

Han et al., "Data Mining: Concepts and Techniques", Second Edition, Chapter 6, 2006, pp. 285-382.
Denisko et al., "Classification and interaction in random forests", PNAS, 2018, vol. 115, No. 8, pp. 1690-1692.
Karimi et al., "Generation and Interpretation of Temporal Decision Rules", International Journal of Computer Information Systems and Industrial Management Applications, vol. 3, pp. 1-17.
LeCun et al., "Convolutional Networks for Images, Speech, and Time-Series", The Handbook of Brain Theory and Neural Networks, 1995, pp. 1-14.
Vapnik, "An Overview of Statistical Learning Theory", IEE Transactions on Neural Networks, vol. 10, No. 5, 1999, pp. 988-999.
Cristianini et al., "An Introduction to Support Vector Machines and other kernal-based learning methods", Cambridge University Press, 2000, pp. 1-4.
Karatzoglou et al., "Support Vector Machines in R", Journal of Statistical Software, 2006 ,vol. 15, Issue 9, pp. 1-28.
Joyce et al., "Bayes' Theorem", The Stanford Encyclopedia of Philosophy, Spring 2019 Ed., Metaphysics Research Lab, Stanford University, 2003, pp. 1-16.
Extended European Search Report and Search Opinion received for European Application No. 23756988.4, mailed on Aug. 29, 2025, 11 pages.
Ulate-Campos et al., "Automated seizure detection systems and their effectiveness for each type of seizure", Seizure, vol. 40, 2016, pp. 88-101.

* cited by examiner

SYSTEMS AND METHODS FOR VAGUS NERVE MONITORING AND STIMULATION

TECHNICAL FIELD

The present disclosure generally relates to devices, systems, and methods for detecting, monitoring, predicting, and/or treating medical conditions (e.g., epileptic seizures) using one or more sensors configured to collect biomarker data from a human subject (e.g., vagal tone and/or physiological or other biomarkers).

BACKGROUND

The vagus nerve, also known as the tenth cranial nerve, cranial nerve X, or simply CN X, is a cranial nerve that interfaces with the parasympathetic control of the heart, lungs, and digestive tract. To be precise, the vagus nerve comprises two nerves: the left and right vagus nerves; however, these nerves have historically been referred to collectively as a single subsystem. The vagus is the longest nerve of the autonomic nervous system (ANS) in the human body and comprises both sensory and motor fibers. It supplies motor parasympathetic fibers to all the organs (except the adrenal glands), from the neck down to the second segment of the transverse colon.

The vagus nerve plays an important role in the regulation of multiple physiological processes because it supplies motor parasympathetic fibers to all the organs (except the adrenal glands), from the neck down to the second segment of the transverse colon, and controls several skeletal muscles (e.g., muscles of the larynx, pharynx, and tongue). As a result, the vagus nerve is responsible for such varied tasks as heart rate, gastrointestinal peristalsis, sweating, and multiple muscle movements in the mouth, including those necessary for speech. Furthermore, parasympathetic innervation of the heart is partially controlled by the vagus nerve, and vagal and spinal ganglionic nerves mediate the lowering of heart rate in humans and other mammals.

Prior studies have found that vagus nerve stimulation ("VNS") may be used treat some medical conditions, such as epilepsy and clinical depression. However, many current VNS stimulation devices must be surgically implanted in the chest of a patient, along with a wired electrode used to stimulate the vagus nerve. Typically, the electrode will be implanted in proximity to the left vagus nerve. The right vagus nerve is not used because it is more likely to carry fibers that supply nerves to the heart. When activated, the implanted device applies electrical stimulation to the left vagus nerve, via the electrode, triggering activity in several areas of the brain. Noninvasive VNS devices have recently been developed and approved for some clinical applications (e.g., to treat cluster headaches and pain). However, conventional implanted and noninvasive VNS devices are generally open-loop systems, with little or no feedback to inform dosing/titration outside of patient tolerability and, in some cases, ictal tachycardia sensing to detect the possible onset of an epileptic seizure.

BRIEF SUMMARY OF EXEMPLARY ASPECTS

In view of the shortcomings of prior systems, there exists need for noninvasive, less invasive, and/or closed-loop devices and systems that can detect and/or monitor vagus nerve signals, alone or in combination with other biomarkers (e.g., collected using one or more sensors), and utilize this biomarker data, e.g., to modulate VNS therapy and thereby provide improved clinical benefits. For example, the present disclosure contemplates devices and systems that use a variety of implanted and/or external sensors to collect biomarker data that may be used to determine vagal tone (sympathetic versus parasympathetic), and/or the onset, duration, and classification of seizures. In some aspects, such devices and systems may also be used to predict that a seizure is imminent or likely to occur in a subject (e.g., within a predefined period of time, such as within 15, 30, 45, or 60 seconds). In some aspects, these devices and systems are configured to analyze the collected biomarker data using computational analyses, including without limitation simple linear regression, multiple non-linear regression, and in some cases complex machine learning and/or artificial intelligence algorithms (e.g., neural networks). As explained herein, devices and systems according to the disclosure may be configured to use the collected biomarker data (alone or processed using any of the algorithms described herein) to detect other potential health issues, and to use this information as feedback to adjust the stimulation being provided by a VNS component of such devices and/or systems.

In still further aspects, the present devices and systems may also be used to provide feedback to other devices or systems intended to control epilepsy and/or modulate vagal tone (e.g., a deep brain stimulator, or a responsive neuromodulation system), or to provide feedback that can be used by a patient or medical professional to select or modify a medical treatment (e.g., a medical professional may determine that a patient should be administered an anti-seizure medication if it is predicted that a seizure is likely or imminent).

In a first general aspect, the disclosure provides a monitoring system (e.g., for the detection, prediction, and/or classification of seizures. An exemplary monitoring system may comprise, e.g., a first set of sensors, comprising an electroencephalogram ("EEG") sensor, a heart rate sensor (e.g., comprising a microphone, an inertial measurement unit ("IMU"), and/or an electrocardiogram ("ECG") sensor); and/or an electromyography ("EMG") sensor, wherein the first set of sensors is configured to detect, measure, and/or monitor one or more biomarkers of the human subject; and a controller, comprising a processor and memory, communicatively linked to the first set of sensors. In some aspects, the controller is configured to (a) detect that the human subject is experiencing a seizure, (b) predict a likelihood of the human subject experiencing a seizure within a predetermined period of time, and/or (c) classify a seizure experienced by the human subject, based on the one or more biomarkers detected, measured, and/or monitored by the first set of sensors. In some aspects, the predetermined time period comprises exactly, about, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, or 120 seconds, or a range bounded by any pair of the foregoing time points. In other aspects, the predetermined time period may comprise exactly, about, or at least 1, 1.5, 2, 2.5 3, 3.5, 4, 4.5, 5, 5.5, 6, 6.5, 7, 7.5, 8, 8.5, 9, 9.5, or 10 minutes, or a range bounded by any pair of the foregoing time points.

In some aspects, the system further comprises a second set of sensors, comprising a photoplethysmogram ("PPG") sensor, a blood pressure sensor, a respiration sensor, and/or an inertial motion sensor, wherein the second set of sensors is configured to detect, measure, and/or monitor one or more biomarkers of the human subject; wherein the controller is communicatively linked to the second set of sensors and further configured to (a) detect that the human subject is experiencing a seizure, (b) predict a likelihood of the human subject experiencing a seizure within a predetermined period of time, and/or (c) classify a seizure experienced by the human subject, based on the one or more biomarkers detected, measured, and/or monitored by the second set of sensors.

In some aspects, the monitoring system may comprise at least one pupilometer configured to obtain pupil size data from the human subject and communicatively linked to the controller, optionally wherein the pupilometer is at least partially integrated into a housing configured to be worn on a head of a human subject. In some aspects, the housing is configured to rest on a bridge of a nose of the human subject. In some aspects, the housing is configured to rest on a bridge of a nose of the human subject and comprises (a) two temple members configured to secure the housing on the head of the human subject, or (b) a headband or other means configured to secure the housing on the head of the human subject.

In aspects where a pupilometer is used, the system may comprise a controller configured to (a) detect that the human subject is experiencing a seizure, (b) predict a likelihood of the human subject experiencing a seizure within a predetermined period of time, and/or (c) classify a seizure experienced by the human subject, based on the pupil size data obtained using the pupilometer, the one or more biomarkers detected, measured, and/or monitored by the first set of sensors, and/or the one or more biomarkers detected, measured, and/or monitored by the second set of sensors.

In some aspects, the system may further comprise one or more environmental sensors, e.g., configured to measure or detect light (e.g., ambient light) or a temperature, and data provided by such sensors may be used to detect, predict, and/or classify a seizure experienced by the human subject. Such sensors may be incorporated into any of the exemplary aspects set forth herein.

In some aspects, the EEG sensor comprises one or more electrodes connected to at least one of the two temple members; the ECG sensor comprises one or more electrodes connected to at least one of the two temple members; the EMG sensor comprises one or more electrodes connected to the housing by a lead, or is positioned within a second housing and communicatively linked to the controller by a wireless connection; and/or the second set of sensors comprises one or more implantable or external sensors.

In some aspects, the first set of sensors and/or the second set of sensors comprises one or more sensors communicatively linked to the controller by a wireless connection.

In some aspects, the EEG sensor, the ECG sensor, and/or the EMG sensor comprises one or more electrodes connected to the housing by one or more leads.

In some aspects, the controller is at least partially integrated into the housing. In others, it may be positioned within a separate housing (e.g., and communicatively linked to the pupilometer and/or one or more sensors of the first or second sets of sensors, via a wired or wireless connection).

In some aspects, the controller is configured to (a) detect that the human subject is experiencing a seizure, (b) predict a likelihood of the human subject experiencing a seizure within a predetermined period of time, and/or (c) classify a seizure experienced by the human subject, using a machine learning algorithm. In some aspects, the controller is configured to detect, predict, or classify a seizure based on the detection of a 15, 16, 17, 18, 19, 20, 21, 22, 23, 24, or 25% increase in hear rate within 5, 6, 7, 8, 9, 10, 11, 12, 13, 14, or 15 seconds (e.g., detected using a heart rate sensor such as an ECG sensor). In some aspects, the controller is configured to detect, predict, or classify a seizure based on the detection of 0.1 to 1.0 mm change in pupil size (e.g., detected and/or measured using a pupilometer). In some aspects, a seizure may be detected, predicted, or classified based on a pupil size change of 0.1, 0.2, 0.3, 0.4, 0.5, 0.6, 0.7, 0.8, 0.9, or 1.0 mm, or a change within a range defined by any pair of the foregoing values.

In some aspects, the biomarkers detected, measured, and/or monitored by the first set of sensors comprise: a) an electrical signal indicative of brain activity of the human subject; b) an electrical signal indicative of heart activity of the human subject; and/or c) an electrical signal indicative of skeletal muscle activity of the human subject.

In some aspects, the biomarkers detected, measured, and/or monitored by the second set of sensors comprise: a) a heart rate of the human subject; b) a blood pressure of the human subject; c) a respiration rate or respiration cycle of the human subject; and/or d) a position, orientation and/or motion of the human subject.

In some aspects, the controller is further configured to predict a likelihood of the human subject experiencing a seizure within a predetermined period of time, e.g., within the next 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 seconds, within the next 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes, or within a time range bounded by any pair of the foregoing values. In some aspects, the controller may also determine a confidence level or score associated with any prediction disclosed herein.

In some aspects, the controller is further configured to classify seizures experienced by the human subject based on a type or a severity level. In some aspects, the seizure classification is based on a scale, e.g., the Seizure Severity Questionnaire ("SSQ"), the Liverpool Seizure Severity Scale ("LSSS"), the National Hospital Seizure Severity Scale ("NHS3"), or another scale. In some aspects, the controller is configured to receive seizure classification data from the subject, from a medical professional, or from a remote server or other electronic device, for one or more prior seizures detected by the controller, and to use this seizure classification data to classify subsequent seizures detected by the controller. For example, the seizure classification data may comprise a seizure classification determined using any of the foregoing scales, and an analysis of the seizure classification and one or more sensor signals collected using one or more sensors of the present systems may be used to identify a baseline or range that correlates with an associated seizure classification. Similarly, a classifier implemented by the controller may be trained using recorded sensor signals obtained from one or more sensors of the present systems during or prior to a seizure, and one or more corresponding seizure classifications).

In some aspects, the controller is further configured to store seizure history data in the memory, wherein the seizure history data is based on a time of occurrence, a type, and/or a severity level, of detected seizures.

In some aspects, the controller is further configured to generate a textual, audio, and/or visual indicator when the controller predicts that a seizure is imminent, or likely to occur within a period of time (e.g., within the next 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 45, or 60 seconds, or within a time range bounded by any pair of the foregoing values). This indicator may, e.g., be provided to the human subject or to a medical professional or other party (e.g., the indicator may be displayed to the human subject and transmitted to a medical professional via a wired or wireless connection). In some aspects, the human subject may also be alerted to take action in advance of a predicted seizure (e.g., an alert may direct the subject to sit or lie down).

In some aspects, the system further comprises an external or implantable stimulator comprising at least one electrode capable of delivering electrical stimulation to the vagus nerve; wherein the controller is communicatively linked to the stimulator and further configured to activate, modulate, and/or terminate stimulation after detecting that the human subject is experiencing a seizure or predicting a likelihood of the human subject experiencing a seizure within a predetermined time period. In some aspects, the activation, modulation, and/or termination of stimulation may be based on a detected or predicted seizure severity level. In some aspects, the controller is configured to reduce or terminate stimulation upon detecting a change in heart rate of 1, 2, 3, 4, 5, 6, or 7% (or a change within a range defined by any pair of the foregoing percentages) during stimulation, as this may indicate an undesirable side effect. The change in heart rate may be measured against a baseline value (e.g., determined prior to stimulation).

In a second general aspect, the disclosure provides a method of monitoring seizures experienced by a human subject, comprising: obtaining a first set of biomarkers for the human subject using a first set of sensors, comprising an EEG sensor, a heart rate sensor (e.g., comprising a microphone, an IMU, and/or an ECG sensor); and/or an EMG sensor, wherein the first set of sensors is configured to detect, measure, and/or monitor one or more biomarkers of the human subject; and analyzing the first set of biomarkers using a controller comprising a processer and memory, wherein the analysis comprises (a) detecting that the human subject is experiencing a seizure, (b) predicting a likelihood of the human subject experiencing a seizure within a predetermined time period, and/or (c) classifying a seizure experienced by the human subject, based on the first set of biomarkers.

In some aspects, the method further comprises obtaining a second set of biomarkers for the human subject using a second set of sensors, comprising a PPG sensor, a blood pressure sensor, a respiration sensor, and/or an inertial motion sensor, wherein the second set of sensors is configured to detect, measure, and/or monitor one or more biomarkers of the human subject; and wherein the analyzing step further comprises analyzing the second set of biomarkers using the controller, and the analysis further comprises (a) detecting that the human subject is experiencing a seizure, (b) predicting a likelihood of the human subject experiencing a seizure within a predetermined time period, and/or (c) classifying a seizure experienced by the human subject, based on the first set of biomarkers, and the second set of biomarkers.

In some aspects, the method further comprises measuring a pupil size of the human subject using at least one pupilometer communicatively linked to the controller, optionally wherein the pupilometer is at least partially integrated into a housing configured to be worn on the head of the human subject. In some aspects, the housing is configured to rest on a bridge of a nose of the human subject and comprises two temple members configured to secure the housing on the head of the human subject. In aspects where a pupilometer is used, such methods may further comprise: analyzing the measured pupil size, and the steps of (a) detecting that the human subject is experiencing a seizure, (b) predicting a likelihood of the human subject experiencing a seizure within a predetermined time period, and/or (c) classifying a seizure experienced by the human subject, may be based on any combination of the measured pupil size, the first set of biomarkers, and/or the second set of biomarkers.

In some aspects, a method according to the disclosure may further comprise a step of obtaining light (e.g., ambient light) and/or temperature data from one or more environmental sensors, and data provided by such sensors may be used to detect, predict, and/or classify a seizure experienced by the human subject. Such sensors may be incorporated into any of the exemplary methods set forth herein.

In some aspects, the EEG sensor comprises one or more electrodes connected to at least one of the two temple members; the ECG sensor comprises one or more electrodes connected to at least one of the two temple members; the EMG sensor comprises one or more electrodes connected to the housing by a lead, or is positioned within a second housing and communicatively linked to the controller by a wireless connection; and/or the second set of sensors comprises one or more implantable or external sensors.

In some aspects, the EEG sensor, the ECG sensor, and/or the EMG sensor comprises one or more electrodes connected to the housing by one or more leads.

In some aspects, the controller is at least partially integrated into the housing.

In some aspects, the controller is configured to (a) detect that the human subject is experiencing a seizure, (b) predict a likelihood of the human subject experiencing a seizure, and/or (c) classify a seizure experienced by the human subject, using a machine learning algorithm and the measured pupil size, in combination with the first set of biomarkers and/or the second set of biomarkers.

In some aspects, the first set of sensors and/or the second set of sensors comprises one or more sensors communicatively linked to the controller by a wireless connection.

In some aspects, the biomarkers detected, measured, and/or monitored by the first set of sensors comprises: a) an electrical signal indicative of brain activity of the human subject; b) an electrical signal indicative of heart activity of the human subject; and/or c) an electrical signal indicative of skeletal muscle activity of the human subject.

In some aspects, the biomarkers detected, measured, and/or monitored by the second set of sensors comprises: a) a heart rate of the human subject; b) a blood pressure of the human subject; c) a respiration rate or respiration cycle of the human subject; and/or d) a position, orientation and/or motion of the human subject.

In some aspects, the controller is further configured to predict a likelihood of the human subject experiencing a seizure within a defined period of time.

In some aspects, the controller is further configured to classify seizures experienced by the human subject based on a type or a severity level.

In some aspects, the controller is further configured to store seizure history data in the memory, wherein the seizure history data is based on a time of occurrence, a type, and/or a severity level, of detected seizures.

In some aspects, the controller is further configured to alert the human subject using a textual, audio and/or visual indicator when the controller predicts that a seizure is imminent, or likely to occur within a predetermined period of time. In some aspects, the controller is further configured to transmit an alert comprising an textual, audio, and/or visual indicator to a medical professional when the controller predicts that a seizure is imminent, or likely to occur within the predetermined period of time.

In some aspects, the method further comprises: stimulating a vagus nerve of the human subject using an external or implantable stimulator comprising at least one electrode capable of delivering electrical stimulation to the vagus nerve; wherein the controller is communicatively linked to the stimulator and further configured to activate, modulate, and/or terminate stimulation (a) after detecting that the human subject is experiencing a seizure or (b) based on a prediction that that the human subject is likely to experience a seizure.

In a third general aspect, the disclosure provides devices that may be used to monitor or treat a human subject for the occurrence of seizures (e.g., to reduce the duration or severity of detected or predicted seizures, or to stop a predicted seizure from occurring). A device according to the disclosure may comprise a head-worn housing that contains and/or communicates with one or more sensors configured to monitor biomarkers of a human subject (e.g., in connection with the systems and methods described herein). For example, the device may comprise a head-worn housing (e.g., structured as a pair of glasses or goggles, or as a headset). The head-worn housing may be configured to rest on the nose and to be secured via temple members to the ears, or held in place by a strap worn around the human subject's head. The device may comprise one or more pupilometers configured to measure a pupil size of the human subject. Additional sensors may be integrated into or connected to the housing (e.g., one or more electrical leads may connect electrodes to the housing (e.g., to detect and/or obtain EEG, EKG, or EMG biomarkers for the human subject). A controller, comprising a processor and memory, may be integrated into the housing and configured to receive and process sensor data from one or more communicatively linked sensors (e.g., any type of sensor described herein). In some aspects, the controller may receive and process the pupil size and biomarker data collected from a one or more additional sensors. The controller may be configured to detect, predict, and/or classify seizures experienced by the human subject based upon the received pupil size and biomarker data. To avoid any doubt, it is understood that the controller of a head-worn device described herein may be configured to perform any step, process, or function of the systems and methods described in further detail herein.

It is expressly understood that any structure, element, parameter, or function described in the foregoing summary of exemplary aspects may be incorporated into any other exemplary aspect listed above or otherwise disclosed herein. For example, a sensor or parameter used in one exemplary system may be integrated into another exemplary system, without departing from the spirit of the present disclosure. Such permutations are contemplated but not expressly recited in the interests of brevity. Similarly, any structure, element, parameter, or function described in connection with an exemplary aspect may be removed or omitted in still further exemplary aspects.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

Figure 1:
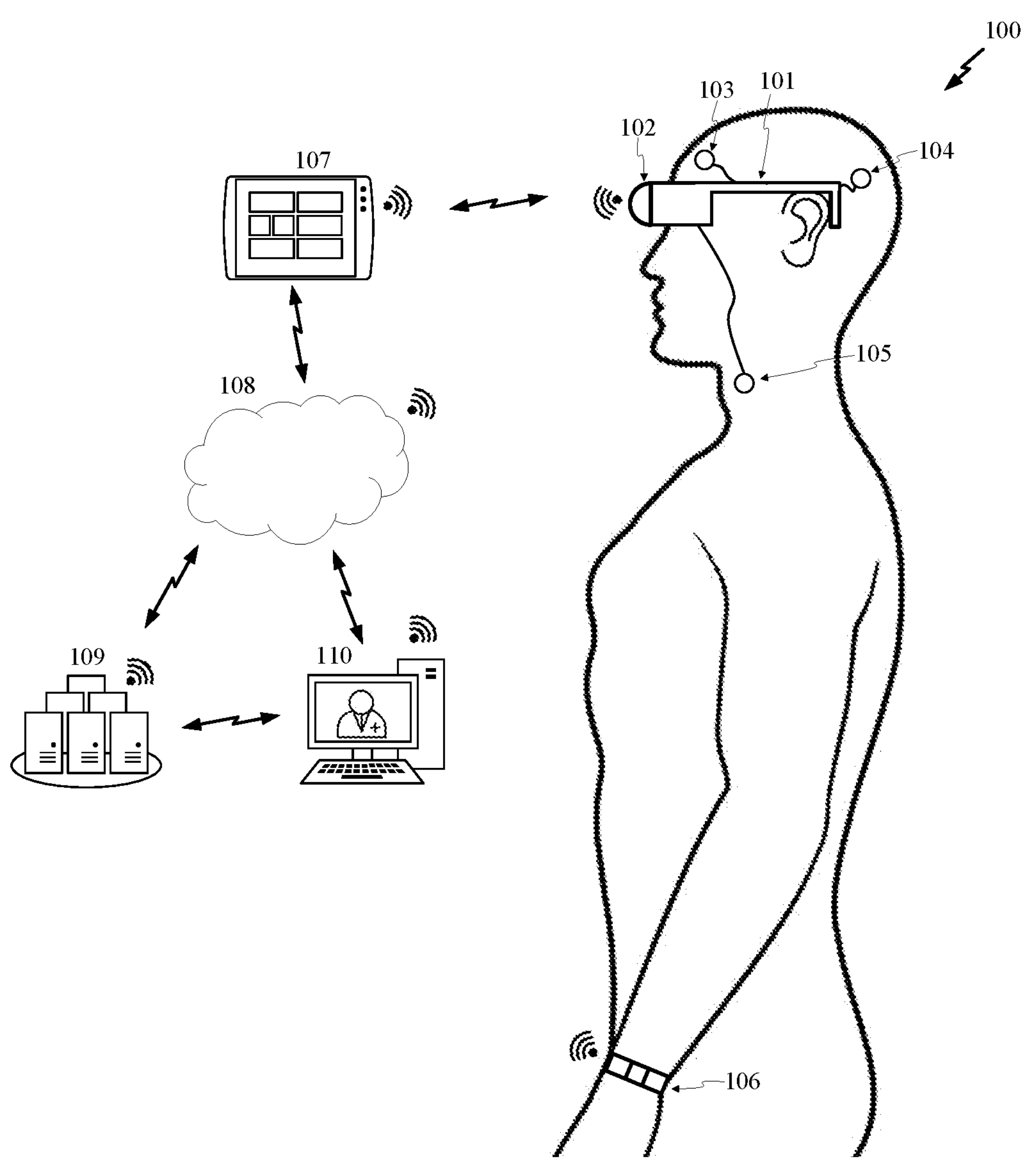
FIG. 1 is a diagram illustrating an exemplary aspect of a system for monitoring and treating an epileptic subject using a head-worn device comprising a controller configured to detect, analyze, and/or monitor biomarker signals obtained from several external and/or implanted sensors. In this example, the system comprises pupilometer (integrated into the head-worn housing), as well as one or more EEG, ECG, and EMG electrodes. Optional cloud-based components of a system according to the disclosure are also illustrated.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several exemplary aspects according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary aspects, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

As noted above, the present disclosure is generally directed to devices, systems and methods for detecting, predicting, and classifying seizures experienced by a human subject. In some aspects, such devices, systems, and methods may also be used to treat the human subject (e.g., by reducing the duration or severity of a seizure or stopping the occurrence of a predicted seizure) using VNS. In still further aspects, the present devices, systems, and methods may be used to control epilepsy and/or modulate vagal tone (e.g., for deep brain stimulation, or a responsive neuromodulation system), or to evaluate pharmaceutical agents or regimens intended to treat epilepsy or modify vagal tone.

There are currently few validated options for monitoring and determining the occurrence of a seizure, e.g., EEG and electrocorticography ("ECoG"). As such, clinicians typically rely on patient journaling to track seizure frequency, duration, and intensity to determine if therapeutic interventions are effective. Such journaling has proven to be inaccurate and presents logistical issues (e.g., a patient cannot maintain an accurate journal for night-time events that occur while the patient is sleeping). The few validated measures (i.e., EEG and ECoG) are not typically ambulatory, and are usually captured in clinic or even in hospital, and thus yield a mere snapshot in time of seizure activity, which can be highly variable. Furthermore, with the exception of surgical recission of seizure foci, therapies intended to reduce seizure impact (anti-epileptic drugs and neuromodulation devices) often take weeks to months to demonstrate their effect. Thus, determining seizure frequency, duration and intensity (collectively "seizure impact") for monitoring purposes outside of the clinic presents a challenge for patients and medical caregivers.

Validated devices and systems for epilepsy are known and capable of detecting ictal tachycardia using a single ECG electrode of an implanted device (which has the advantage of being mobile with the user and always on), and such devices may be used to guide treatment (e.g., a boost in the stimulation amplitude may be automatically delivered in an effort to reduce the duration and/or intensity of a seizure. However, not every epileptic seizure is accompanied by ictal tachycardia, false positive triggers of a stimulation boost are frequent, and tachycardia occurs after seizure onset, so a boost in therapy typically does not prevent the seizure from happening altogether. Thus, there is a need for both more accurate seizure detection, and ideally accurate seizure prediction, for both reporting purposes and therapy modulation/titration.

The present devices, systems, and methods provide a solution to this problem, among other benefits and improvements over the prior art. For example, they may be used to accurately detect and predict seizures in real-time, and the collected biomarkers may be used to close the loop and provide feedback to therapy in terms of dose adjustment and timing. For example, if seizure onset, or imminent onset is detected, not only can this be recorded for monitoring purposes, but the human subject and/or their caregiver or clinician may be alerted for the purposes of modifying behavior and making a therapeutic adjustment (e.g., taking a fast acting medication, or increasing or otherwise changing the dose of neuromodulation therapy being delivered).

Apart from providing feedback for monitoring and therapy dosing in an epileptic patient, the detection of seizures and of side effects may also help significantly during the titration phase when the optimal therapeutic dose for a subject is being determined. Patients beginning a course of therapy often start on a low dose and up-titrate to a therapeutic optimum. In some cases, the rate of titration is determined by the rate of reduction in seizure impact (frequency, intensity, duration), while in others (e.g., VNS) the titration rate is further modulated by side effects experienced by the patient, which he or she must adapt to before the dose can be increased. In the example of VNS, the up-titration of electrical dose is rate limited by side effects like dysphagia, pain, hoarseness, cough, etc. When the patient has adapted to a level of stimulation (by their own determination, or that of their clinician) the stimulation is increased until a side effect becomes uncomfortable again, then the adaptation and titration cycle repeats. However, it is also possible to use one or more sensors to monitor side effects (e.g., an EMG sensor for laryngeal activation or voice analysis to detect hoarseness) to determine when a dose may be up-titrated. Additionally, reliable and accurate seizure detection, over whatever timescale is appropriate, can aid in determining when the optimal dose has been achieved.

Unfortunately, when it comes to dose optimization, the typical intra-patient high variability in seizure impact coupled with the long time constant over which some seizure therapies work mean that it can take a long time (months or even years) to determine when the optimal therapeutic dose has been achieved. In these cases, one typically uses a faster acting biomarker that can serve as a proxy for the expected therapeutic outcome. As an example, VNS can be used to treat rheumatoid arthritis, but it can take months to see relief of symptoms and clinically significant change, However, the levels of inflammatory cytokines in the blood, which serve as markers for systemic inflammation, change almost immediately, and simple blood draws can be used to optimize VNS dosing to minimize the level of cytokines in the blood. This is more problematic in the case of epilepsy (and depression) where not many biomarkers for the disease have been identified and/or those that have are not easily measurable and/or they do not change quickly when VNS is initiated.

Some biomarkers that reflect vagal activation (e.g., through stimulation of the vagus nerve by internal or external means) include noradrenaline and acetylcholine. The latter can only be typically measured by sampling brain fluid, but levels of the former can be detected by changes in pupil size through pupillometry. Measures of vagal tone also provide an indirect proxy for potential seizure activity since seizure likelihood increases with an increase sympathetic nervous system imbalance. Heart rate variability ("HRV") and other heart rate ("HR") related measures are the most often cited measures of vagal tone. Lastly, it is also known that most vital signs, such as blood pressure ("BP"), blood oxygen levels ("$SPO_2$"), and respiration show changes associated with seizure activity (and other health related events). Thus, a system that measures several of these parameters on a continuous or even intermittent basis, could collect enough data that, when combined with data collected, by any means, for each seizure occurrence (time, frequency, intensity, duration, seizure type), could, over time, inform a machine learning algorithm that could learn to detect either the occurrence of a seizure, or the likelihood of an imminent seizure or both. That prediction/detection, in turn, could be used to provide feedback to any therapy being deployed to manage seizures in a patient, and/or the behavior of the patient (not going outside for example if a seizure is imminent). For example, an increase in anti-epilepsy drug dose, or administration of a fast-acting drug, or adjusting the stimulation parameters of a neuromodulation device to prevent a seizure or reduce its impact.

The devices, systems, and methods described herein provide various benefits and improvements compared to prior solutions in this area. For example, in some aspects, they utilize a variety of biomarkers (including digital biomarkers), vital signs, and other bio-signals, collected from a variety of sensors, to provide data that may be processed by one or more controllers of a system described herein. In some aspects, they utilize data provided by the sensors to detect an epileptic seizure, classify the seizure type, provide a measure of vagal tone, and/or determine if undesirable side-effects are occurring. Laryngeal EMG signals, detected vocal changes or coughing (e.g., by microphone), bradycardia or other changes in heart rate as detected by one or more ECG electrodes are all examples of undesired side effects that may be detected, but there are several others as well. The sensor data could be analyzed in real time, or in post hoc analysis. This data being also supplied to the system or computational algorithms described above. Note that, apart from detecting vagal tone, seizures and side effects, the sensor data might also be used to titrate the stimulation parameters of the VNS system to improve therapeutic effect and/or reduce side effects.

In some aspects, the present devices, systems, and methods may also utilize other data, not provided by the sensors, but rather provided by the user, a caregiver, physician, or other detectors that are not part of the system (e.g., a heart monitor, digital mental health application or sensors, etc.). This data could be representative of seizures and their characteristics and/or representative of another health event (e.g., an occurrence of atrial fibrillation, or depression, including suicidal thoughts, tinnitus, rheumatoid arthritis flare up, etc.). In particular, any health condition that can be mediated by the autonomic nervous system (and there are many beyond the list provided above) would be of interest to the system, as the VNS stimulation could be improving or worsening those conditions while it attempts to treat epilepsy.

In some aspects, the present devices, systems, and methods utilize machine learning (or other) algorithms, to analyze all or some of the available sensor data in order to identify biomarkers, digital biomarkers, vital signs, and other bio-signals (physiological and behavioral) that correlate with seizure activity, likelihood of imminent seizure activity, vagal tone, and/or other health issues (for example anxiety, depression, heart failure, and many others). Said algorithm determining 'signatures' in the data that represent an event such as a seizure, and/or a likely imminent seizure (based on analysis of data preceding event signatures), and potentially classify that event by seizure type, and/or can also determine when excursions in vagal tone, towards parasympathetic or sympathetic states are large enough to require correction. As an illustrative example, the system might determine that when heart rate increases over a short time scale (e.g., the rate of heart rate increase is high >3 BPS/S), and/or pupil size increases more than 2%, and/or blood pressure increases by more than 10 mmHG, or electroneurography sensors indicate a marked increase in sympathetic nerve activity, that a seizure is imminent or already underway.

In still further aspects, a machine learning system implemented by a controller of a system or device described herein may identify "signatures" for other health events that are not necessarily related to epilepsy, but might be related to vagal tone, or that could be modulated by stimulating the vagus nerve. It should be understood that this disclosure is equally applicable to other stimulation targets of the nervous system (e.g., brain, peripheral nerves, central nerves, etc.). Again, as an example, the system may determine that increased lung congestion as detected by a microphone and/or irregular heartbeats as detected by a ECG electrode(s), and/or reduced blood flow as detected by a flow meter or oxygen detector are signs of onset or worsening of heart failure. As another example, the system may determine that increased stasis, and/or time spent in the prone position as determined by an inertial motion sensor and/or gyroscope are indicative on onset or worsening depression. These detected signatures and/or excursions in vagal tone (as measured by electroneurography as an example) may be used to provide input to a controller for adjusting the stimulus being provided by a system intended to modulate the human autonomic nervous system, such as a VNS device. The stimulation parameters (amplitude, pulse width, duty cycle) could be generally increased to effect better control of epilepsy (reducing the frequency and/or duration of seizures), or generally reduced to in order to reduce/eliminate side effects. Frequency is another stimulation parameter whose directional change could be up or down to effect better disease management and/or eliminate side effects. Note also, that treatment of other health conditions mediated by the ANS may require a general increase or decrease of the stimulation, or other changes in the stimulation paradigm, such as making it intermittent, or changing the stimulation intensity when a subject is at rest.

FIG. 1 is a diagram illustrating an exemplary aspect of a system for monitoring a human subject to detect, predict, and/or classify seizures experienced by the human subject In this example, the system comprises a head-worn housing (101), designed to collect biomarker data from the human subject. In this example, the head-worn housing includes two temple members that extend towards and around the subject's ears in order to secure the housing to the subject's head (e.g., similar to the temple members typically found on a pair of eyeglasses). One or more pupilometers (102) are integrated into the housing (101), and configured to measure a pupil size of the human subject. An additional EEG sensor (103), ECG sensor (104) and EMG sensor (105) are shown, and each comprises one or more electrodes attached to the subject's head and connected to the housing (101). As illustrated by these figures, any of these sensors may be connected to the housing or a portion thereof (e.g., to the temple members).

In this example, a controller comprising a processor and memory is integrated into the housing (101). The controller may be configured to receive, store, and/or process sensor data collected from the one or more pupilometers and any other communicatively linked sensors described herein, e.g., in order to detect, predict, and/or classify a seizure experienced by the human subject (as described in further detail elsewhere herein), or to identify vagal tone or noradrenaline release. In this example, an additional external sensor is provided in the form of an $SpO_2$ sensor (106) integrated into a wrist-worn smartwatch device. The $SpO_2$ sensor is communicatively linked to the controller via a wireless connection. It is understood that in other exemplary aspects, a system as shown in this figure may comprise any other internal or external sensors described herein, in addition to or instead of the sensors shown in this non-limiting example. Biomarkers collected using these sensors may be used by the controller in connection with any of the analyses described herein (e.g., as inputs to be processed by one or more AI, ML or other algorithms).

While not shown in this example, as described elsewhere herein in some aspects a system according to the disclosure may further comprise a vagus nerve stimulator. This stimulator may be at least partially integrated into a second housing implanted in the human subject, which may also include a second controller communicatively linked to the external controller described above (or to another external device). In some aspects, a system may comprise an implanted vagus nerve stimulator in one housing and an implanted controller integrated into a separate implanted housing, e.g., where the implanted vagus nerve stimulator, the implanted controller (and an optional external controller are communicatively linked by one or more wired or wireless connections). For example, an external controller integrated into a head-worn housing may receive biomarker and pupil measurements and communicate with an implanted controller, that in turn communicates with and controls an implanted vagus nerve stimulator. It is contemplated that sensor data may be provided to any combination of implanted or external controllers, and similarly, the processing and analysis of sensor data may be performed by any combination of implanted or external controllers. For example, as illustrated by FIG. 1 the head-worn housing (101) may communicate with an external device (107) and with a remote server (109), or with a computer operated or controlled by a medical professional (110), via the cloud (108). In some aspects, the external device (107) or remote server (109) may comprise a controller configured to process sensor data collected by the present devices and systems. AI and ML models often require substantial computational processing and, as such, it may be more efficient to offload such calculations to a controller of the external device (107) or remote server (109), e.g., to increase processing speed or to conserve the battery life of an implanted controller.

Note that pupil size, in particular, can be indicative of both seizure onset (pupils get larger during a seizure—sometimes asymmetrically) and of VNS stimulation (pupils get larger when a VNS system is stimulating afferent vagus nerve fibers). Thus pupillometry, and the other sensor data collected by the present devices and systems, may be used to both detect seizures, and to provide a titration signal for the VNS system (e.g., increasing VNS will cause a further increase in pupil diameter, providing a measurable proxy for therapeutic impact).

In view of the use of pupil size as a biomarker, it is important to control the variation in pupil size that is due to fluctuations in ambient lighting. Thus, in some aspects the present devices and systema may provide controlled lighting of subject's eye/pupil. This can be accomplished in the head-worn housing by providing adequate shielding of the lenses of the device and optionally also for the sides (including nasal, temporal, cheek, and forehead facing areas), and optionally providing a fixed or variable, but well-controlled intensity light source within the housing. Thus, in some aspects, any surface or region of the housing may be opaque or semi-opaque. In some aspects, a variable light source may be desirable (e.g., to promote pupil dilation or to reduce/maximize the size of an effect caused by the release of a particular biomarker). In some aspects, one or more light senor(s) on or in the housing may be used to measure the ambient light and that data may be used to allow an AI/ML or other algorithm to compensate for fluctuations in ambient light. For example, data comprising an ambient light level may be used to train an AI/ML model or used to normalize or correct one or more other signals obtained by sensors of the present systems.

Biomarkers collected by any internal or external sensors, optionally in combination with additional data provided by the human subject, a caregiver, a medical professional, or other devices (e.g., collected using a smartphone, watch or wearable device), may be aggregated and analyzed by the controller to detect, predict, or classify seizures experiences by the human subject. In some aspects, this analysis may be performed using AI/ML techniques. For example, a system according to the disclosure may receive biomarkers for a human subject from one or several sensors, e.g., including a pupilometer, an EMG sensor positioned near the larynx of the human subject, an ECG sensor integrated into a VNS device (or external to the body), sound data from a microphone, blood pressure data from an external cuff or an implanted sensor, one or more EEG electrodes located on or within the head of the human subject, an inertial sensor implanted in the human subject, a heart-rate sensor, a body-temperature sensor, and an electroneurographic sensor measuring compound evoked potentials on the vagus nerve of the human subject. Any or all of these signals may be used as inputs for an AI/ML or other algorithm, to detect, predict, and/or classify seizures experienced by the human subject. Additional inputs from one or more environmental sensors, e.g., light and/or temperature sensors may improve the accuracy of the output(s) of the AI/ML or other algorithm. Fluctuations in ambient light would affect the pupillometry measurements if the light shielding of the eyes is not absolute, and quick changes in ambient temperature can affect autonomic or vagal tone. Accordingly, in some aspects an ambient light level may be detected and may be used to train an AI/ML model or used to normalize or correct one or more other signals obtained by sensors of the present systems, in connection with any processing algorithm implemented by a controller of the present systems.

In some aspects, a system according to the disclosure may receive result data describing the occurrence of health events (e.g., seizure occurrence and duration, acute heart failure, depressive episodes, worsening rheumatoid arthritis, acute tinnitus etc.). Using each sensor as a potential explanatory variable, the system may be configured to conduct linear regression of each explanatory variable against one result variable and determine the degree of correlation. Discarding those explanatory variables to that do not correlate to the health outcome attempting to be explained, the system could then perform multiple linear regression analysis using the remaining explanatory variables in order to derive a more accurate detection or prediction model. The system may be configured to further test non-linear transformations of one or more explanatory variables (an exponential transform as an example) remaining in the model to determine if a yet more accurate detection or prediction model can be determined. In some aspects, an AI/ML algorithm or model may be used for this purpose.

Once the model is determined, it may be implemented in the system, either in real time, or in a post hoc analysis. In some aspects, a system according to the disclosure may comprise an implanted vagus nerve stimulator and controller, as well as an external controller (e.g., in a head-worn housing) capable of communicating with both the implanted controller and the cloud (or another external device). The model may be stored in the memory of the implanted controller, the external controller, and/or another external devices. The model may be used to determine the occurrence of a seizure (or to predict that a seizure is likely or imminent) and to adjust the stimulation being delivered by the implanted vagus nerve stimulator to prevent or mitigate the seizure or symptoms thereof. In addition, the system may also be configured to log the occurrence and duration of events in a memory residing in the system and this data may be provided to the human subject, to a medical professional, or to another party (e.g., providing an objective record that does not rely on the human subject maintaining an accurate personal log of events)

Figure 2:
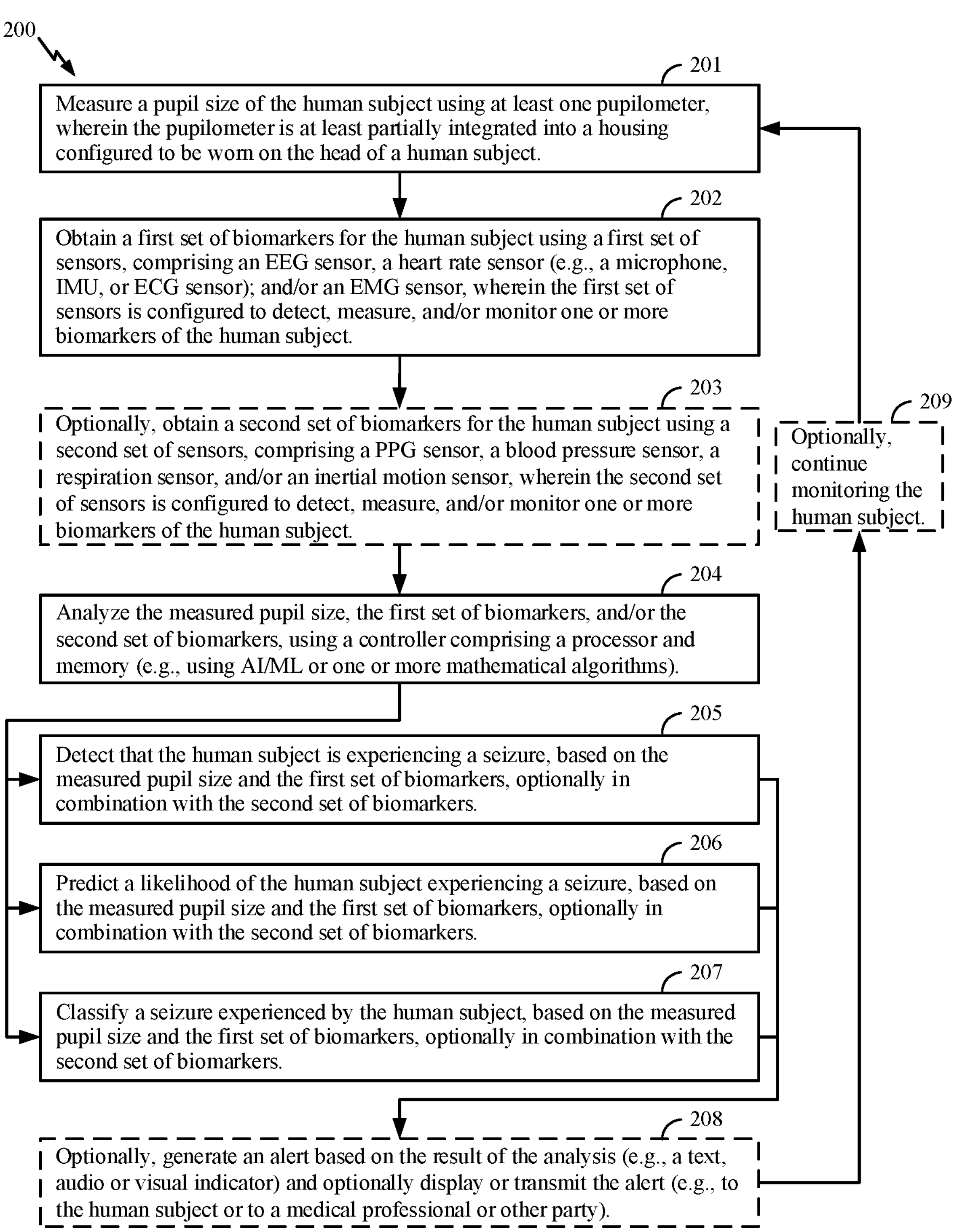
FIG. 2 is a conceptual flow diagram summarizing a general method for detecting, predicting, and/or classifying seizures according to the present disclosure.

FIG. 2 is a conceptual flow diagram summarizing a general method for detecting, predicting, and/or classifying seizures according to the present disclosure. As illustrated by this figure, such methods may begin the measurement of a pupil size of the human subject using at least one pupilometer, wherein the pupilometer is at least partially integrated into a housing configured to be worn on the head of a human subject (201). Before, after, or in parallel with step 201, a first set of biomarkers for the human subject may be obtained using a first set of sensors, comprising an EEG sensor, a heart rate sensor (e.g., an ECG sensor); and/or an EMG sensor, wherein the first set of sensors is configured to detect, measure, and/or monitor one or more biomarkers of the human subject (202). Optionally, a second set of biomarkers for the human subject may be obtained using a second set of sensors, comprising a PPG sensor, a blood pressure sensor, a heart-rate sensor, a body-temperature sensor, a respiration sensor, and/or an inertial motion sensor, wherein the second set of sensors is configured to detect, measure, and/or monitor one or more biomarkers of the human subject (203). Step 203 may also be performed in parallel with or prior to steps 201 or 202.

The pupil size measurement(s) and the other obtained biomarkers may then be analyzed by a controller comprising a processor and memory, e.g., using one or more AI/ML, or other algorithms (204). This analysis may comprise detecting that the human subject is experiencing a seizure (205), predicting a likelihood of the human subject experiencing a seizure (206), and/or classifying a seizure experienced by the human subject (207), based on the measured pupil size and the first set of biomarkers, optionally in combination with the second set of biomarkers (207) and/or the environmental measurements. In some aspects, the system may be configured to generate an alert based on the result of the analysis (208) that can be displayed or transmitted, e.g., displayed to the human subject via a textual, audio, and/or visual indicator and/or transmitted to a medical professional. The system may also be configured to return the monitoring mode (209), e.g., repeating the general process shown in this figure, either after the analysis step, or after the optional alert is generated.

Figure 3:
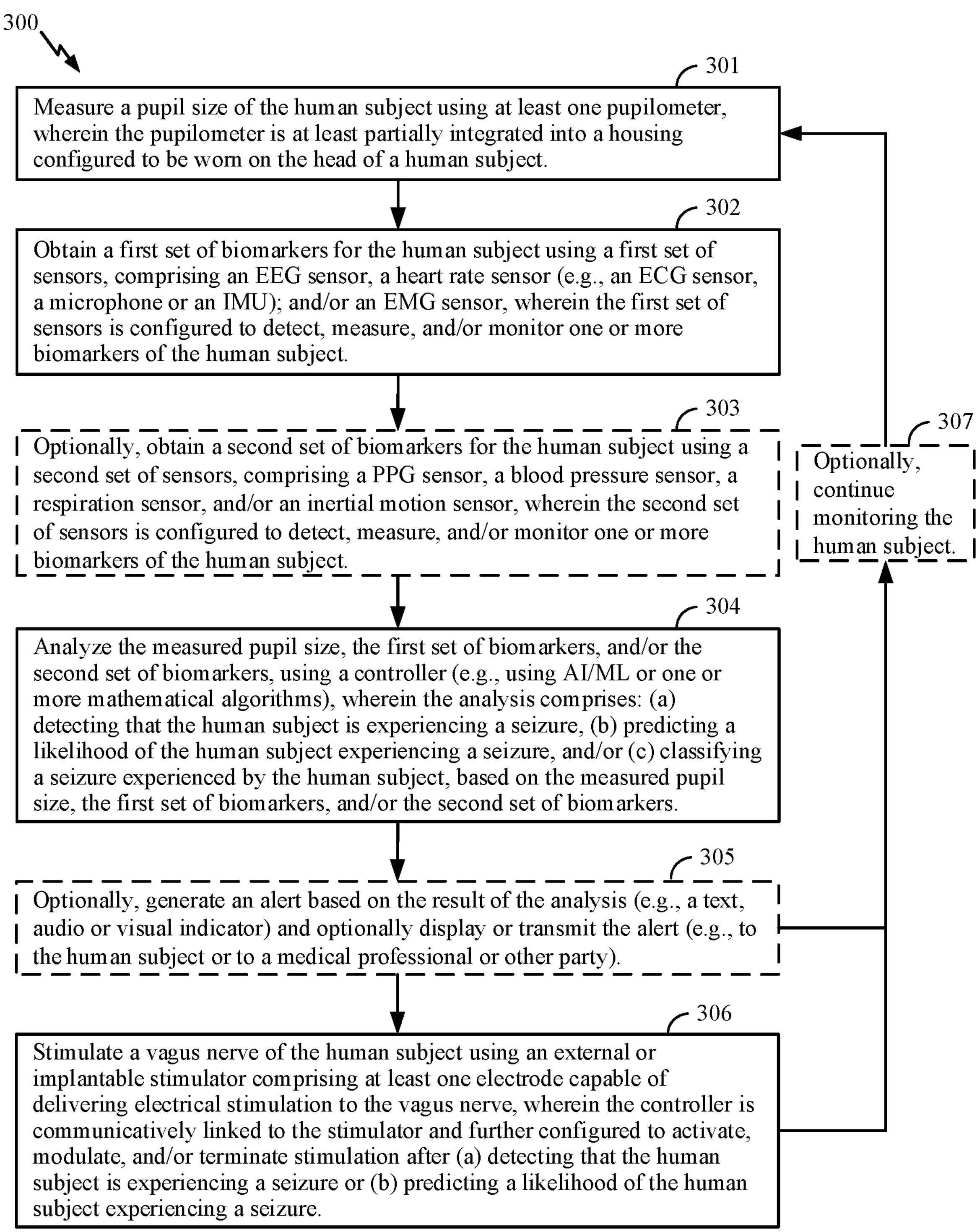
FIG. 3 is a conceptual flow diagram summarizing a general method for treating a human subject using vagus nerve stimulation following the detection or prediction of a seizure, according to the present disclosure. Such treatment may, e.g., be useful as a means to reduce the severity or duration of a seizure, or to stop a predicted seizure from occurring.

FIG. 3 is a conceptual flow diagram summarizing a general method for treating a human subject using VNS following the detection or prediction of a seizure, according to the present disclosure. Such treatment may, e.g., be useful as a means to reduce the severity or duration of a seizure, or to stop a predicted seizure from occurring. As illustrated by this figure, a method for treatment according to the disclosure may perform as described in the context of FIG. 2 (i.e., steps 301-305 are analogous to steps 201-208). However, as shown by FIG. 3, the system may be further configured to stimulate a vagus nerve of the human subject using an external or implantable stimulator comprising at least one electrode capable of delivering electrical stimulation to the vagus nerve, wherein the controller is communicatively linked to the stimulator and further configured to activate, modulate, and/or terminate stimulation (a) after detecting that the human subject is experiencing a seizure or (b) predicting a likelihood of the human subject experiencing a seizure. (i.e., step 306).

Figure 4:
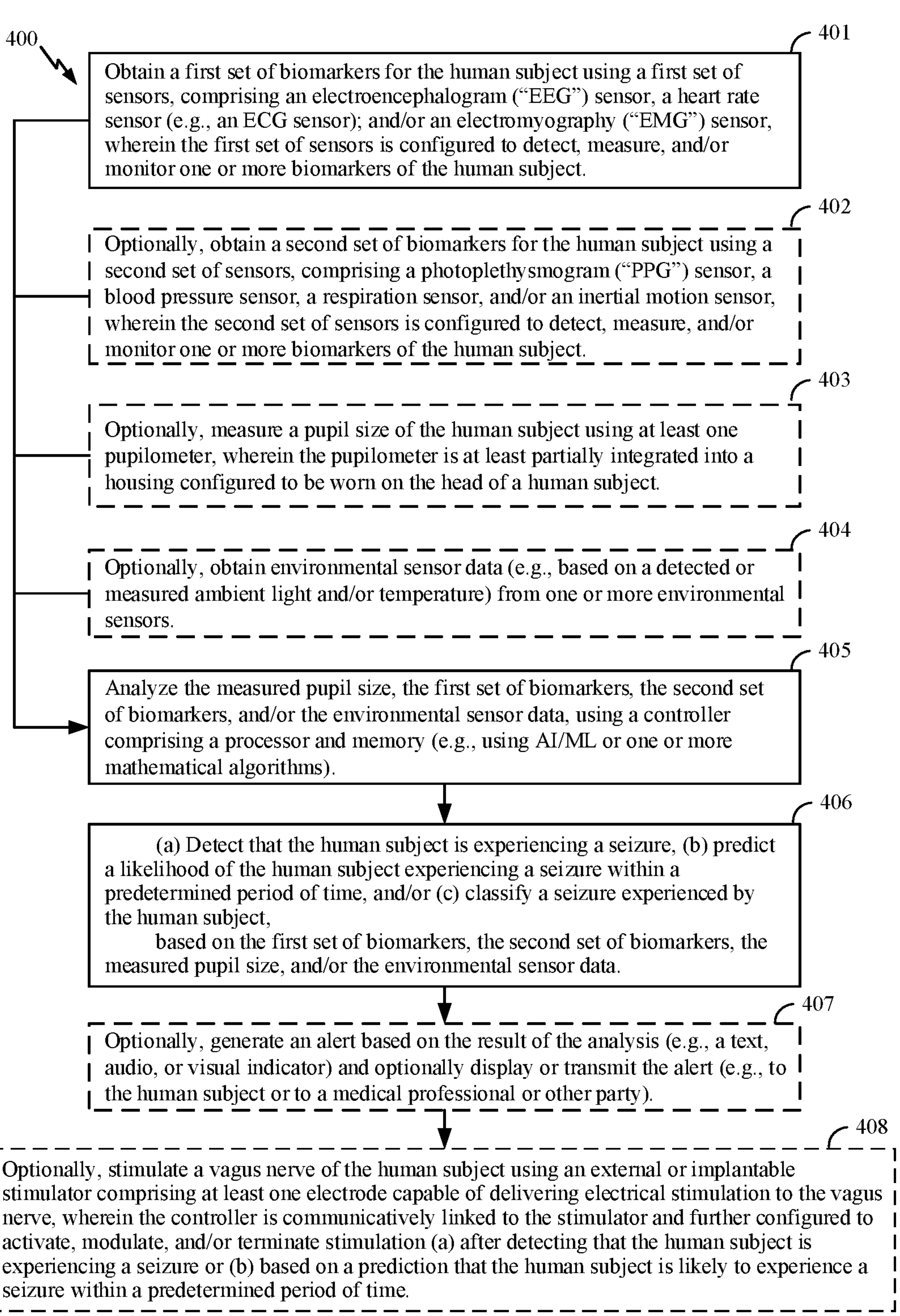
FIG. 4 is a conceptual flow diagram summarizing another general method for detecting, predicting, classifying, and/or treating seizures according to the present disclosure.

FIG. 4 is a conceptual flow diagram summarizing another general method for detecting, predicting, classifying, and/or treating seizures according to the present disclosure. As illustrated by this alternative embodiment, in some aspects, biomarker data may be collected from a first set of sensors (e.g., an EEG sensor, a heart rate sensor, and/or an EMG sensor) and optionally paired with biomarker data collected from a second set of sensors (e.g., a PPG sensor, a blood pressure sensor, a respiration sensor, and or an inertial motion sensor), pupil size measurements (e.g., collected using a pupilometer), and/or environmental sensor data (e.g., comprising ambient light and/or temperature data) (steps 401-404). Any combination of these inputs may be analyzed, e.g., using an algorithm or an AI/ML model (404) in order to detect, predict, and or classify a seizure experienced by the human subject (405). The results of the analysis may then be optionally used to generate an alert (407) and/or to trigger stimulation of a vagus nerve of the human subject (408). Though not shown, it is understood that such methods may also be repeated any number of times as part of a monitoring system (e.g., following step 408, the method may repeat by returning to any of the prior steps, providing continuous monitoring of the human subject).

As explained above, the devices and systems described herein may utilize one or more algorithms, or AI/ML models, to analyze sensor data and to detect, predict, or classify seizures experienced by a human subject. Various data analysis techniques may be used to perform these functions, e.g., simple linear regression models conducted with single explanatory variables, to multiple regression, and even nonlinear regression. However, since the number of possible explanatory variables is high, it may be possible to develop better classifiers or predictive algorithms using machine learning, and specifically machine learning algorithms as support vector machine(s), AdaBoost classifier(s), penalized logistic regression, elastic nets, regression tree system(s), gradient tree boosting system(s), naive Bayes classifier(s), neural nets, Bayesian neural nets, k-nearest neighbor classifier(s), deep learning systems, and random forest classifiers.

The term "classifier," as used herein, refers broadly to a machine learning algorithm such as support vector machine(s), AdaBoost classifier(s), penalized logistic regression, elastic nets, regression tree system(s), gradient tree boosting system(s), naive Bayes classifier(s), neural nets, Bayesian neural nets, k-nearest neighbor classifier(s), deep learning systems, and random forest classifiers. The systems and methods described may use any of these classifiers, or combinations thereof.

A "Classification and Regression Trees (CART)," as used herein, refers broadly to a method to create decision trees based on recursively partitioning a data space so as to optimize one or more metrics, e.g., model performance.

The classification systems used herein may include computer executable software, firmware, hardware, or combinations thereof. For example, the classification systems may include reference to a processor and supporting data storage. Further, the classification systems may be implemented across multiple devices or other components local or remote to one another. The classification systems may be implemented in a centralized system, or as a distributed system for additional scalability. Moreover, any reference to software may include non-transitory computer readable media that when executed on a computer, causes the computer to perform one or more steps.

There are many potential classifiers that can be used by the systems and methods described herein. Machine and deep learning classifiers include but are not limited to AdaBoost, Artificial Neural Network (ANN) learning algorithm, Bayesian belief networks, Bayesian classifiers, Bayesian neural networks, Boosted trees, case-based reasoning, classification trees, Convolutional Neural Networks, decisions trees, Deep Learning, elastic nets, Fully Convolutional Networks (FCN), genetic algorithms, gradient boosting trees, k-nearest neighbor classifiers, LASSO, Linear Classifiers, naive Bayes classifiers, neural nets, penalized logistic regression, Random Forests, ridge regression, support vector machines, or an ensemble thereof. See, e.g., Han & Kamber (2006) Chapter 6, Data Mining, Concepts and Techniques, 2nd Ed. Elsevier: Amsterdam. As described herein, any classifier or combination of classifiers (e.g., an ensemble) may be used by the present systems.

Deep Learning Algorithms

In some aspects, the classifier is a deep learning algorithm. Machine learning is a subset of artificial intelligence that uses a machine's ability to take a set of data and learn about the information it is processing by changing the algorithm as data is being processed. Deep learning is a subset of machine learning that utilizes artificial neural networks inspired by the workings on the human brain. For example, the deep learning architecture may be multilayer perceptron neural network (MLPNN), backpropagation, Convolutional Neural Network (CNN), Recurrent Neural Network (RNN), Long Short-Term Memory (LSTM), Generative Adversarial Network (GAN), Restricted Boltzmann Machine (RBM), Deep Belief Network (DBN), or an ensemble thereof.

Classification Trees

A classification tree is an easily interpretable classifier with built in feature selection. A classification tree recursively splits the data space in such a way so as to maximize the proportion of observations from one class in each subspace.

The process of recursively splitting the data space creates a binary tree with a condition that is tested at each vertex. A new observation is classified by following the branches of the tree until a leaf is reached. At each leaf, a probability is assigned to the observation that it belongs to a given class. The class with the highest probability is the one to which the new observation is classified. Classification trees are essentially a decision tree whose attributes are framed in the language of statistics. They are highly flexible but very noisy (the variance of the error is large compared to other methods).

Tools for implementing classification tree are available, by way of non-limiting example, for the statistical software computing language and environment, R. For example, the R package "tree," version 1.0-28, includes tools for creating, processing and utilizing classification trees. Examples of Classification Trees include but are not limited to Random Forest. See also Kaminski et al. (2017) "A framework for sensitivity analysis of decision trees." *Central European Journal of Operations Research.* 26(1): 135-159; Karimi & Hamilton (2011) "Generation and Interpretation of Temporal Decision Rules", *International Journal of Computer Information Systems and Industrial Management Applications*, Volume 3, the content of which is incorporated by reference in its entirety.

Random Forest Classifiers

Classification trees are typically noisy. Random forests attempt to reduce this noise by taking the average of many trees. The result is a classifier whose error has reduced variance compared to a classification tree. Methods of building a Random Forest classifier, including software, are known in the art. Prinzie & Poel (2007) "Random Multiclass Classification: Generalizing Random Forests to Random MNL and Random NB." *Database and Expert Systems Applications. Lecture Notes in Computer Science.* 4653; Denisko & Hoffman (2018) "Classification and interaction in random forests." *PNAS* 115(8): 1690-1692, the contents of which are incorporated by reference in its entirety.

To classify a new observation using the random forest, classify the new observation using each classification tree in the random forest. The class to which the new observation is classified most often amongst the classification trees is the class to which the random forest classifies the new observation. Random forests reduce many of the problems found in classification trees but at the tradeoff of interpretability.

Tools for implementing random forests as discussed herein are available, by way of non-limiting example, for the statistical software computing language and environment, R. For example, the R package "random Forest," version 4.6-2, includes tools for creating, processing and utilizing random forests.

AdaBoost (Adaptive Boosting)

AdaBoost provides a way to classify each of n subjects into two or more categories based on one k-dimensional vector (called a k-tuple) of measurements per subject. AdaBoost takes a series of "weak" classifiers that have poor, though better than random, predictive performance and combines them to create a superior classifier. The weak classifiers that AdaBoost uses are classification and regression trees (CARTs). CARTs recursively partition the dataspace into regions in which all new observations that lie within that region are assigned a certain category label. AdaBoost builds a series of CARTs based on weighted versions of the dataset whose weights depend on the performance of the classifier at the previous iteration. See Han & Kamber (2006) *Data Mining, Concepts and Techniques,* 2nd Ed. Elsevier: Amsterdam, the content of which is incorporated by reference in its entirety. AdaBoost technically works only when there are two categories to which the observation can belong. For $g>2$ categories, $(g/2)$ models must be created that classify observations as belonging to a group or not. The results from these models can then be combined to predict the group membership of the particular observation. Predictive performance in this context is defined as the proportion of observations misclassified.

Convolutional Neural Network

Convolutional Neural Networks (CNNs or ConvNets) are a class of deep, feed-forward artificial neural networks, most commonly applied to analyzing visual imagery. CNNs use a variation of multi-layer perceptrons designed to require minimal preprocessing. They are also known as shift invariant or space invariant artificial neural networks (SIANN), based on their shared-weights architecture and translation invariance characteristics. Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. CNNs use relatively little preprocessing compared to other image classification algorithms This means that the network learns the filters that in traditional algorithms were hand-engineered. This independence from prior knowledge and human effort in feature design is a major advantage. LeCun and Bengio (1995) "Convolutional networks for images, speech, and time-series," in Arbib (Ed.), The Handbook of Brain Theory and Neural Networks, MIT Press, the content of which is incorporated by reference in its entirety. Fully convolutional indicates that the neural network is composed of convolutional layers without any fully-connected layers or MLP usually found at the end of the network. Convolutional Neural Network is an example of deep learning.

Support Vector Machines

Support vector machines (SVMs) are recognized in the art. In general, SVMs provide a model for use in classifying each of n subjects to two or more categories based on one k-dimensional vector (called a k-tuple) per subject. An SVM first transforms the k-tuples using a kernel function into a space of equal or higher dimension. The kernel function projects the data into a space where the categories can be better separated using hyperplanes than would be possible in the original data space. To determine the hyperplanes with which to discriminate between categories, a set of support vectors, which lie closest to the boundary between the disease categories, may be chosen. A hyperplane is then selected by known SVM techniques such that the distance between the support vectors and the hyperplane is maximal within the bounds of a cost function that penalizes incorrect predictions. This hyperplane is the one which optimally separates the data in terms of prediction. Vapnik (1998) *Statistical Learning Theory*; Vapnik "An overview of statistical learning theory" *IEEE Transactions on Neural Networks* 10(5): 988-999 (1999) the content of which is incorporated by reference in its entirety. Any new observation is then classified as belonging to any one of the categories of interest, based where the observation lies in relation to the hyperplane. When more than two categories are considered, the process is carried out pairwise for all of the categories and those results combined to create a rule to discriminate between all the categories. See Cristianini, N., & Shawe-Taylor, J. (2000). *An Introduction to Support Vector Machines and Other Kernel-based Learning Methods*. Cambridge: Cambridge University Press provides some notation for support vector machines, as well as an overview of the method by which they discriminate between observations from multiple groups.

In an exemplary embodiment, a kernel function known as the Gaussian Radial Basis Function (RBF) is used. Vapnik, 1998. The RBF may be used when no a priori knowledge is available with which to choose from a number of other defined kernel functions such as the polynomial or sigmoid kernels. See Han et al. *Data Mining: Concepts and Techniques*, Morgan Kaufman 3rd Ed. (2012). The RBF projects the original space into a new space of infinite dimension. A discussion of this subject and its implementation in the R statistical language can be found in Karatzoglou et al. "Support Vector Machines in R," *Journal of Statistical Software* 15(9) (2006), the content of which is incorporated by reference in its entirety. All SVM statistical computations described herein were performed using the statistical software programming language and environment R 2.10.0. SVMs were fitted using the ksvm( ) function in the kernlab package. Other suitable kernel functions include, but are not limited to, linear kernels, radial basis kernels, polynomial kernels, uniform kernels, triangle kernels, Epanechnikov kernels, quartic (biweight) kernels, tricube (triweight) kernels, and cosine kernels. Support vector machines are one out of many possible classifiers that could be used on the data. By way of non-limiting example, and as discussed below, other methods such as naive Bayes classifiers, classification trees, k-nearest neighbor classifiers, etc. may be used on the same data used to train and verify the support vector machine.

Naïve Bayes Classifier

The set of Bayes Classifiers are a set of classifiers based on Bayes' Theorem. See, e.g., Joyce (2003), Zalta, Edward N. (ed.), "Bayes' Theorem", *The Stanford Encyclopedia of Philosophy* (Spring 2019 Ed.), Metaphysics Research Lab, Stanford University, the content of which is incorporated by reference in its entirety.

Classifiers of this type seek to find the probability that an observation belongs to a class given the data for that observation. The class with the highest probability is the one to which each new observation is assigned. Theoretically, Bayes classifiers have the lowest error rates amongst the set of classifiers. In practice, this does not always occur due to violations of the assumptions made about the data when applying a Bayes classifier.

The naïve Bayes classifier is one example of a Bayes classifier. It simplifies the calculations of the probabilities used in classification by making the assumption that each class is independent of the other classes given the data. Naïve Bayes classifiers are used in many prominent anti-spam filters due to the ease of implantation and speed of classification but have the drawback that the assumptions required are rarely met in practice. Tools for implementing naive Bayes classifiers as discussed herein are available for the statistical software computing language and environment, R. For example, the R package "e1071," version 1.5-25, includes tools for creating, processing and utilizing naive Bayes classifiers.

Neural Networks

One way to think of a neural network is as a weighted directed graph where the edges and their weights represent the influence each vertex has on the others to which it is connected. There are two parts to a neural network: the input layer (formed by the data) and the output layer (the values, in this case classes, to be predicted). Between the input layer and the output layer is a network of hidden vertices. There may be, depending on the way the neural network is designed, several vertices between the input layer and the output layer.

Neural networks are widely used in artificial intelligence and data mining but there is the danger that the models the neural nets produce will over fit the data (i.e., the model will fit the current data very well but will not fit future data well). Tools for implementing neural nets as discussed herein are available for the statistical software computing language and environment, R. For example, the R package "e1071," version 1.5-25, includes tools for creating, processing and utilizing neural nets.

k-Nearest Neighbor Classifiers (KNN)

The nearest neighbor classifiers are a subset of memory-based classifiers. These are classifiers that have to "remember" what is in the training set in order to classify a new observation. Nearest neighbor classifiers do not require a model to be fit.

To create a k-nearest neighbor (knn) classifier, the following steps are taken:

1. Calculate the distance from the observation to be classified to each observation in the training set. The distance can be calculated using any valid metric, though Euclidian and Mahalanobis distances are often used. The Mahalanobis distance is a metric that takes into account the covariance between variables in the observations.
2. Count the number of observations amongst the k nearest observations that belong to each group.
3. The group that has the highest count is the group to which the new observation is assigned.

Nearest neighbor algorithms have problems dealing with categorical data due to the requirement that a distance be calculated between two points but that can be overcome by defining a distance arbitrarily between any two groups. This class of algorithm is also sensitive to changes in scale and metric. With these issues in mind, nearest neighbor algorithms can be very powerful, especially in large data sets. Tools for implementing k-nearest neighbor classifiers as discussed herein are available for the statistical software computing language and environment, R. For example, the R package "e1071," version 1.5-25, includes tools for creating, processing and utilizing k-nearest neighbor classifiers.

Training Data

In another aspect, methods described herein include training of about 75%, about 80%, about 85%, about 90%, or about 95% of the data in the library or database and testing the remaining percentage for a total of 100% data. In an aspect, from about 70% to about 90% of the data is trained and the remainder of about 10% to about 30% of the data is tested, from about 80% to about 95% of the data is trained and the remainder of about 5% to about 20% of the data is tested, or from about 90% of the data is trained and the remainder of about 10% of the data is tested.

In some aspects, the database or library contains data from the analysis of over about 25, about 60, over about 125, over about 250, over about 500, or over about 1000 human subjects The training data may comprise, e.g., data relating to any of the parameters described herein, e.g., biomarker data collected from one or more sensors.

Methods of Classification

The disclosure provides for methods of classifying data (e.g., biomarker data collected from one or more sensors) obtained from a human subject in order to detect, predict, or classify seizures experienced by the human subject. In some aspects, these methods involve preparing or obtaining training data, as well as evaluating test data obtained from an individual (as compared to the training data), using one of the classification systems including at least one classifier as described above. Preferred classification systems use classifiers such as, but not limited to, support vector machines (SVM), AdaBoost, penalized logistic regression, naive Bayes classifiers, classification trees, k-nearest neighbor classifiers, Deep Learning classifiers, neural nets, random forests, Fully Convolutional Networks (FCN), Convolutional Neural Networks (CNN), and/or an ensemble thereof. Deep Learning classifiers are a more preferred classification system. The classification system may be configured, e.g., to output a determination as to whether a seizure is detected, likely or imminent, or to classify a detected seizure, based on biomarkers collected from one or more of the sensors described herein.

As noted above, in some aspects a classifier may comprise an ensemble of multiple classifiers. For example, an ensemble method may include SVM, AdaBoost, penalized logistic regression, naive Bayes classifiers, classification trees, k-nearest neighbor classifiers, neural nets, FCN, CNN, Random Forests, deep learning, or any ensemble thereof, in order to make any of the determinations, classifications, or predictions described herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A monitoring system, comprising:

one or more sensors, comprising an electroencephalogram ("EEG") sensor; a heart rate sensor; and/or an electromyography ("EMG") sensor, wherein the one or more sensors is configured to detect, measure, and/or monitor one or more biomarkers of the human subject;

a housing, configured to be worn on a head of the human subject;

a light sensor, integrated into the housing and configured to detect a signal indicative of an ambient light level;

at least one pupillometer, integrated into the housing and configured to detect a signal indicative of a pupil size of the human subject; and a controller, comprising a processor and memory, communicatively linked to the one or more sensors, the light sensor, and the at least one pupillometer, wherein the controller is configured to (a) determine an ambient light level based on the signal detected by the light sensor;

(b) determine a pupil size of the human subject, based on the signal detected by the pupillometer;

(c) determine a normalized pupil size measurement for the human subject, based on the ambient light level and the pupil size of the human subject; and (d) predict a likelihood of the human subject experiencing a seizure within a predetermined time period, and a classification of the seizure, using one or more pre-trained classifiers, based on (i) the one or more biomarkers detected, measured, and/or monitored by the one or more sensors, and (ii) the normalized pupil size measurement.

2. The system of claim 1, further comprising:

a second one or more sensors, comprising a photoplethysmogram ("PPG") sensor, a blood pressure sensor, a respiration sensor, and/or an inertial motion sensor, wherein the second one or more sensors is configured to detect, measure, and/or monitor one or more biomarkers of the human subject;

wherein the controller is communicatively linked to the second one or more sensors and further configured to predict a likelihood of the human subject experiencing a seizure within a predetermined time period, and a classification of the seizure, using one or more pre-trained classifiers, based on (i) the one or more biomarkers detected, measured, and/or monitored by the one or more sensors, and (ii) the normalized pupil size measurement; and (iii) the one or more biomarkers detected, measured, and/or monitored by the second one or more sensors.

3. The system of claim 2, wherein the one or more sensors and/or the second one or more sensors comprises one or more sensors communicatively linked to the controller by a wireless connection.

4. The system of claim 2, wherein the biomarkers detected, measured, and/or monitored by the second one or more sensors comprises:

a) a heart rate of the human subject;

b) a blood pressure of the human subject;

c) a respiration rate or respiration cycle of the human subject; and/or d) a position, orientation and/or motion of the human subject.

5. The system of claim 1, wherein the controller is further configured to predict a likelihood of the human subject experiencing a seizure within a predetermined period of time comprising a) the next 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 seconds;

b) the next 1, 2, 3, 4, or 5 minutes; and/or c) a time range bounded by any pair of time points listed in a) or b).

6. The system of claim 5, wherein the controller is configured to transmit a text, audio, and/or visual alert to a local, mobile, or remote electronic device, computer, or server, owned or operated by a hospital or medical professional, when the controller predicts a likelihood of the human subject experiencing a seizure within the predetermined period of time.

7. The system of claim 1, wherein the housing is configured to rest on a bridge of a nose of the human subject and comprises two temple members configured to secure the housing on the head of the human subject.

8. The system of claim 1, wherein the EEG sensor comprises one or more electrodes connected to at least one of the two temple members;

the heart rate sensor comprises a microphone, an inertial measurement unit ("IMU"), and/or an ECG sensor comprising one or more electrodes connected to at least one of the two temple members;

the EMG sensor comprises one or more electrodes connected to the housing by a lead, or is positioned within a second housing and communicatively linked to the controller by a wireless connection; and/or the second one or more sensors comprises one or more implantable or external sensors.

9. The system of claim 1, wherein the EEG sensor, the heart rate sensor, and/or the EMG sensor comprises one or more electrodes connected to the housing by one or more leads.

10. The system of claim 1, wherein the controller is at least partially integrated into the housing.

11. The system of claim 1, wherein the biomarkers detected, measured, and/or monitored by the one or more sensors comprise:

a) an electrical signal indicative of brain activity of the human subject;

b) an electrical signal indicative of heart activity of the human subject; and/or c) an electrical signal indicative of skeletal muscle activity of the human subject.

12. The system of claim 1, wherein the controller is further configured to classify seizures experienced by the human subject based on type or severity level.

13. The system of claim 1, wherein the controller is further configured to store seizure history data in the memory, wherein the seizure history data is based on a time of occurrence, a type, and/or a severity level, of detected seizures.

14. The system of claim 1, wherein the controller is further configured to alert the human subject using a textual, audio and/or visual indicator when the controller predicts that a seizure is imminent, or likely to occur within a period of time.

15. The system of claim 1, wherein the controller is further configured to transmit seizure history data to a local, mobile, or remote electronic device, computer, or server, wherein the seizure history data is based on a time of occurrence, a type, and/or a severity level, of detected seizures.

16. The system of claim 1, wherein the local or remote electronic, device, computer, or server is owned or operated by a hospital or a medical professional.

17. The system of claim 1, wherein the system further comprises an external or implantable stimulator comprising at least one electrode capable of delivering electrical stimulation to the vagus nerve;

wherein the controller is communicatively linked to the stimulator and further configured to activate, modulate, and/or terminate stimulation after detecting that the human subject is experiencing a seizure or based on the likelihood of the human subject experiencing a seizure.

18. A method of monitoring seizures experienced by a human subject, comprising:

obtaining a first set of biomarkers for the human subject using one or more sensors, comprising an electroencephalogram ("EEG") sensor, a heart rate sensor; and/or an electromyography ("EMG") sensor, wherein the one or more sensors is configured to detect, measure, and/or monitor one or more biomarkers of the human subject; and detecting a signal indicative of an ambient light level, from a light sensor integrated into a housing worn on the head of the humans subject;

detecting a signal indicative of a pupil size of the human subject, using at least one pupillometer integrated into the housing worn on the head of the humans subject;

determining an ambient light level based on the signal detected by the light sensor, and a pupil size of the human subject, based on the signal detected by the pupillometer;

determining a normalized pupil size measurement for the human subject, based on the ambient light level and the pupil size of the human subject; and predicting a likelihood of the human subject experiencing a seizure within a predetermined time period, and a classification of the seizure, using one or more pre-trained classifiers, based on (i) the one or more biomarkers detected, measured, and/or monitored by the one or more sensors, and (ii) the normalized pupil size measurement.

19. The method of claim 18, further comprising:

obtaining a second set of biomarkers for the human subject using a second one or more sensors, comprising a photoplethysmogram ("PPG") sensor, a blood pressure sensor, a respiration sensor, and/or an inertial motion sensor, wherein the second one or more sensors is configured to detect, measure, and/or monitor one or more biomarkers of the human subject; and wherein the controller is further configured to predict the likelihood of the human subject experiencing a seizure within a predetermined time period, and a classification of the seizure, using one or more pre-trained classifiers, based on (i) the one or more biomarkers detected, measured, and/or monitored by the one or more sensors, and (ii) the normalized pupil size measurement, and (iii) the one or more biomarkers detected, measured, and/or monitored by the second one or more sensors.

20. The method of claim 19, wherein the EEG sensor comprises one or more electrodes connected to at least one of the two temple members;

the heart rate sensor comprises a microphone, an IMU, or an ECG sensor comprising one or more electrodes connected to at least one of the two temple members;

the EMG sensor comprises one or more electrodes connected to the housing by a lead, or is positioned within a second housing and communicatively linked to the controller by a wireless connection; and/or the second one or more sensors comprises one or more implantable or external sensors.

21. The method of claim 20, wherein the EEG sensor, the ECG sensor, and/or the EMG sensor comprises one or more electrodes connected to the housing by one or more leads.

22. The method of claim 19, wherein the housing is configured to rest on a bridge of a nose of the human subject and comprises two temple members configured to secure the housing on the head of the human subject.

23. The method of claim 19, wherein the controller is at least partially integrated into the housing.

24. The method of claim 19, wherein the one or more sensors and/or the second one or more sensors comprises one or more sensors communicatively linked to the controller by a wireless connection.

25. The method of claim 19, wherein the biomarkers detected, measured, and/or monitored by the second one or more sensors comprises:

a) a heart rate of the human subject;

b) a blood pressure of the human subject;

c) a respiration rate or respiration cycle of the human subject; and/or d) a position, orientation and/or motion of the human subject.

26. The method of claim 19, wherein the controller is further configured to store seizure history data in the memory, wherein the seizure history data is based on a time of occurrence, a type, and/or a severity level, of detected seizures.

27. The method of claim 19, wherein the controller is further configured to alert the human subject using a text, audio, and/or visual indicator when the controller predicts that a seizure is imminent, or likely to occur within the predetermined period of time.

28. The method of claim 19, wherein the controller is further configured to alert the human subject using a text, audio, and/or visual indicator when the controller predicts that a seizure is likely to occur within the next 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds.

29. The method of claim 19, wherein the method further comprises stimulating a vagus nerve of the human subject using an external or implantable stimulator comprising at least one electrode capable of delivering electrical stimulation to the vagus nerve;

wherein the controller is communicatively linked to the stimulator and further configured to activate, modulate, and/or terminate stimulation (a) after detecting that the human subject is experiencing a seizure or (b) based on predicting the likelihood of the human subject experiencing a seizure.

30. The method of claim 18, wherein the biomarkers detected, measured, and/or monitored by the one or more sensors comprises:

a) an electrical signal indicative of brain activity of the human subject;

b) an electrical signal indicative of heart activity of the human subject; and/or c) an electrical signal indicative of skeletal muscle activity of the human subject.

31. The method of claim 18, wherein the controller is further configured to predict a likelihood of the human subject experiencing a seizure within a predetermined time period comprising:

a) the next 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 seconds;

b) the next 1, 2, 3, 4, or 5 minutes; and/or c) a time range bounded by any pair of time points listed in a) or b).

* * * * *